United States Patent [19]
Ideker et al.

[11] Patent Number: 5,522,854
[45] Date of Patent: Jun. 4, 1996

[54] METHOD AND APPARATUS FOR THE PREVENTION OF ARRHYTHMIA BY NERVE STIMULATION

[75] Inventors: Raymond E. Ideker, Birmingham, Ala.; Xiaohong Xhou, Durham, N.C.

[73] Assignee: Duke University, Durham, N.C.

[21] Appl. No.: 245,980

[22] Filed: May 19, 1994

[51] Int. Cl.$^6$ ................................................ A61N 1/36
[52] U.S. Cl. .................... 607/6; 607/5; 607/14; 607/72; 128/702; 128/705
[58] Field of Search ............... 607/4–6, 14, 48, 607/118, 119, 72; 128/702, 704, 705

[56] References Cited

U.S. PATENT DOCUMENTS

| | | | |
|---|---|---|---|
| 5,042,497 | 8/1991 | Shapland | 607/6 X |
| 5,203,326 | 4/1993 | Collins | 607/4 |
| 5,265,617 | 11/1993 | Verrier et al. | 128/704 |

OTHER PUBLICATIONS

D. R. Bolick et al.; *Quantitative analysis of myocardial infarct structure in patients with ventricular tachycarida*, Circulation 74, pp. 1266–1279 (1986).

Ying Xia, et al; *Roles of Opioid Peptides of Pag in Analogous Electro–Acupuncture Inhibition of Experimental Arrhythmia: Analyzed by Specific Antisera Microinjection*, Acupuncture & Electro–Therapeutics Res., Int. J. 11, pp. 191–198 (1986).

Xia Ying et al; *Inhibitory Effect of Analogous Electro–Acupuncture on Sympathetic Cardiovascular Response to Stimulation of Hypothalamic Defence Area in Rabbits*, Journal of Traditional Chinese Medicine 7(3), pp. 211–214 (1987).

F. Lombardi et al; *Heart Rate Variability as an Index of Sympathovagal Interaction After Acute Myocardial Infarction*, The American Journal of Cariology 60, pp. 1239–1245 (1987).

W. Brent Tarver et al; *Clinical Experience with a Helical Bipolar Stimulating Lead*, PACE 15, pp. 1545–1556 (1992).

X. Zhou et al; Abstract Form; *Afferent Nerve Stimulation Prevents the Increase in Ventricular Arrhythmias caused by Hypothalamic Stimulation in Ischemic Rabbit Hearts*, NASPE®Dated Dec. 3, 1992.

X, Zhou, et al; Abstract Form; *Afferent Nerve Stimulation Decreases Ventricular Arrhythmias Induced by Hypothalamic Stimuation In Rabbits*, American College of Cardiology 42nd Annual Scientific Session, dated Mar. 14–18, 1993.

Primary Examiner—William E. Kamm
Assistant Examiner—Jeffrey R. Jastrzab
Attorney, Agent, or Firm—Bell, Seltzer, Park & Gibson

[57] ABSTRACT

Arrhythmia is prevented by detecting a high risk of arrhythmia and then stimulating afferent nerves to prevent the arrhythmia. By monitoring the sympathetic and parasympathetic nerve activity of a patient the risk of arrhythmia may be assessed. An apparatus for monitoring of parasympathetic and sympathetic nerve activity and stimulating the afferent nerves may be implanted in a patient. Furthermore, the apparatus and method for the prevention of arrhythmia may be combined with apparatus for the treatment of arrhythmia through electric shock to facilitate treatment and prevent reoccurrence of arrhythmia.

16 Claims, 2 Drawing Sheets

METHOD AND APPARATUS FOR THE PREVENTION OF ARRHYTHMIA BY NERVE STIMULATION

This invention was made with government support under Grant No. 28429 ordered by the National Institutes of Health. The government has certain rights in the invention.

FIELD OF THE INVENTION

The present invention relates to the treatment and prevention of arrhythmia. More specifically the present invention relates to implantable apparatus for preventing arrhythmia before it occurs and for treating such arrhythmia in the event that prevention is ineffective.

BACKGROUND OF THE INVENTION

Sudden cardiac death afflicts approximately 300,000 people in the United States every year, and is one of the most pressing health problems in the world (R. Myerburg et al., *Circulation* 85, 1–10 (1992)). Most sudden cardiac deaths are caused by malignant ventricular arrhythmias. Malignant ventricular arrhythmias which lead to death are often triggered by emotional changes, especially stress and fear, during myocardial ischemia and infarction.

Historically, the hypothalamus has been credited with the major control of cardiovascular responses associated with emotions, stress, and defense in both humans and animals. Karplus and Kreidl first demonstrated that electric stimulation of the hypothalamus can cause discharges in many portions of the sympathetic nervous system (J. Karplus and A. Kreidl, *Pflugers Archiv.* 129, 138 (1909)). Stimulation of the hypothalamus can induce tachyarrhythmias in both normal and ischemic animal ventricles (see, e.g., C. Carpeggiani et al., *Circ. Res.* 70, 600 (1992); J. Skinner and J. Reed, *Am. J. Physiol.* 240, H156 (1981)). The activities of the cardiovascular centers in the brain can be modulated by afferent nerve stimulation (see, e.g., L. Renaud et al., *Brain Res. Bull.* 20, 771 (1988); X. Ying et al., *Acta Physiol. Sinica* 36, 133 (1984)). A few reports suggest that stimulation of afferent nerves can reduce the arrhythmias induced by hypothalamic stimulation in normal rabbits (Y. Xia et al., *J. Tradit. chin. Med.* 7, 211 (1987); Y. Xia et al., *J. Acupunc. Electro-therap. Res.* 11, 191 (1986)). However, there is a continued need for new methods and implantable apparatus for preventing arrhythmia before it occurs, and for treating such arrhythmia in the event that prevention is ineffective.

SUMMARY OF THE INVENTION

A first aspect of the present invention is a method of combating heart arrhythmia in a subject. The method comprises monitoring the ratio of sympathetic nerve activity to parasympathetic nerve activity in said subject, detecting a high risk of arrhythmia in said subject based on the ratio of sympathetic and parasympathetic nerve activity, and stimulating afferent nerves in said subject upon detection of a high risk of arrhythmia.

The method may further comprise the steps of determining whether or not the stimulation has prevented an arrhythmia in the subject, and halting an arrhythmia which has occurred by delivery of an electric pulse when the stimulation has not prevented the arrhythmia (e.g., by continuously stimulating the afferent nerves to prevent the reoccurrence of an arrhythmia after delivery of an electric pulse to halt the arrhythmia).

The method may also comprise the steps of determining if an occurring arrhythmia is ventricular tachycardia, and stimulating the afferent nerves during occurrence of the arrhythmia when the arrhythmia is ventricular tachycardia.

A second aspect of the present invention is an implantable apparatus for combating heart arrhythmia in a subject. The apparatus comprises a monitor for monitoring the ratio of sympathetic nerve activity to parasympathetic nerve activity in said subject, a detector for detecting a high risk of arrhythmia in said subject based on said ratio of sympathetic nerve activity to parasympathetic nerve activity, and an electrical stimulator responsive to said detector for stimulating afferent nerves in said subject upon detection of a high risk of arrhythmia.

In a particular embodiment of the foregoing, the apparatus further includes a determining apparatus or device that serves as a means for determining whether or not the stimulation has prevented an arrhythmia in the subject, a stimulator serving as an electric pulse means for halting an arrhythmia which has occurred by delivery of an electric pulse to the subject, and a control circuit or system for controlling the electric pulse means to halt the arrhythmia when the determining means determines that the stimulation did not prevent the arrhythmia (e.g., by delivery of a shock or electric pulse effective to halt the arrhythmia). The electrical stimulator may optionally be configured for continuously stimulating the afferent nerves to prevent the reoccurrence of an arrhythmia after delivery of the electric pulse.

The apparatus may also include a discriminator for determining if an occurring arrhythmia is ventricular tachycardia, wherein the controller controls the stimulator to stimulate the afferent nerves when the discriminator determines that the arrhythmia detected is a ventricular tachycardia.

DETAILED DESCRIPTION OF THE PREFERRED EMBODIMENTS

A first embodiment of an implantable apparatus for carrying out the present invention typically includes a first monitor for monitoring sympathetic nerve activity in the subject, a second monitor for monitoring parasympathetic nerve activity in the subject, a comparator connected to the first and second monitors for providing a comparison of the sympathetic and the parasympathetic nerve activity in the subject, a detector responsive to the comparator for detecting a high risk of arrhythmia in the subject based on the comparison of sympathetic and parasympathetic nerve activity, and an electrical stimulator responsive to the detector for stimulating afferent nerves in the subject upon detection of a high risk of arrhythmia.

The afferent nerves which are to be stimulated by the apparatus are preferably afferent to the heart, particularly heart nerve tissue, or may be afferent to the central nervous system.

The apparatus is sealed in a sterile container (e.g. a hermetically sealed container), and the container is configured so that a pair of monitoring leads can be electrically connected to the first and second monitors, and one or more stimulating leads can be electrically connected to the electrical stimulator. The apparatus is optionally, but preferably, be configured for implantation in the body of a subject a human subject, as an implantable container.

The apparatus of the invention preferably includes circuitry for determining whether or not the stimulation delivered to the afferent nerves has prevented an arrhythmia in the subject, a stimulator serving as an electric pulse means for halting an arrhythmia which has occurred by delivery of an electric pulse to the subject, and a control circuit or system for controlling the electric pulse means to halt the arrhythmia when the determining means determines that the stimulation did not prevent the arrhythmia (e.g., by delivery of a shock or electric pulse effective to halt the arrhythmia by techniques such as anti-tachycardia pacing, large cardioversion, and defibrillation shock). The electrical stimulator may be configured for continuously, or intermittently, stimulating the afferent nerves to prevent the reoccurrence of an arrhythmia after delivery of the electric pulse.

The apparatus preferably includes circuitry serving as a discrimination means responsive to the determining means for determining if an occurring arrhythmia is,ventricular tachycardia. The control means is configured to control the stimulation means to stimulate the afferent nerves when the discrimination means determines the arrhythmia is ventricular tachycardia.

Figure 1:
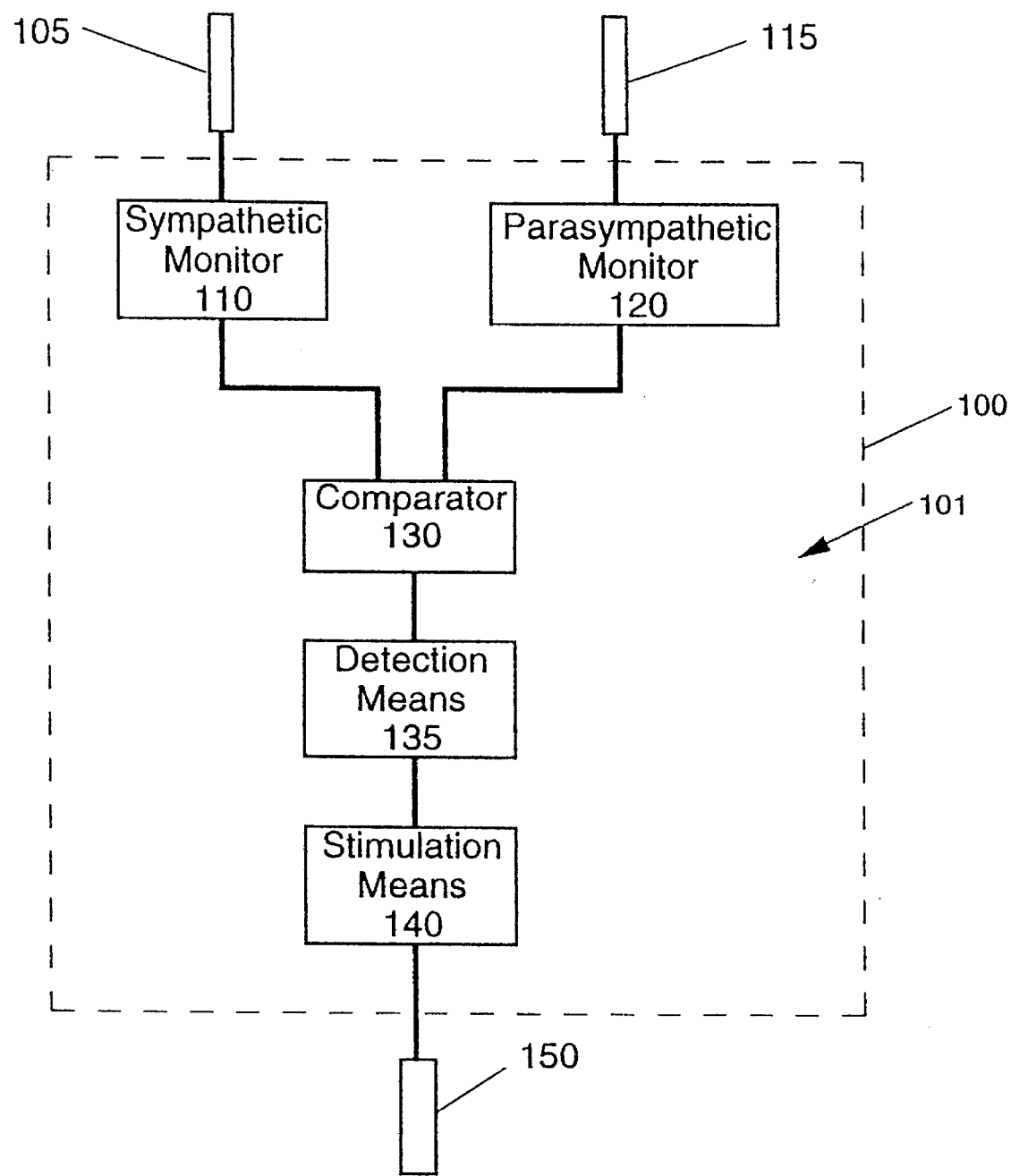
FIG. 1 schematically illustrates an apparatus for the prevention of arrhythmia according to the present invention.

FIG. 1 schematically illustrates one embodiment of the present invention. As seen in FIG. 1, an implantable arrhythmia prevention apparatus 100 is depicted having electronic circuitry 101. The electric circuitry 101 includes a monitoring device 110 for monitoring the sympathetic nerve activity via a lead 105 appropriately positioned to detect electrical activity in the sympathetic nerves. The electronic circuitry 101 further includes a detection device 120 for monitoring the parasympathetic nerve activity via a lead 115 appropriately positioned to detect electrical activity in the parasympathetic nerves. As will be understood by one of skill in this art and discussed further below, the monitoring devices 110 and 120 may use any one of a number of means for monitoring the ratio of sympathetic to parasympathetic activity. The monitoring devices 110 and 120 may sense the electrical voltage present in the respective nerves or may sense the current present in the respective nerves by any number of traditional monitoring methods. Furthermore, the output of the monitoring devices 110 and 120 may be either digital or analog.

In a particularly preferred embodiment of the present invention, a preferred way to measure the ratio of sympathetic to parasympathetic nerve activity is to measure heart rate variability, as will be appreciated by those skilled in the art, with a decrease in heart rate variability indicating an increased risk of the onset of arrhythmia. See, e.g., F. Lombardi et al., Heart Rate variability as an Index of Sympathovagal Interaction After Acute Myocardial Infarction, *Am. J. Cardiol.* 60, 1239 (1987). Apparatus for measuring heart rate variability is known, an example being the MEDIC MONITOR ANS-R1000™(manufactured by ANSAR Inc., 242 South Eighth Street, Philadelphia, Pa. 19017; Tel. (215) 922-6088).

As may be further seen in FIG. 1, the electronic circuitry 101 further includes a comparator 130 operatively associated with the monitoring devices 110 and 120 for comparing the levels of parasympathetic and sympathetic nerve activity detected by the monitoring means 110 and 120. Comparator 130 compares the levels of activity of the parasympathetic and sympathetic nerves and provides that result to the detector 135 which determines if a high probability of an arrhythmia exists. The detector may be a programmable microprocessor which detects a reduction of heart rate variability beyond a predetermined threshold, with a reduction of heart rate variability beyond that threshold indicating that the patient is at risk or at a high probability for the onset of an arrhythmia. If the detector 135 determines that a high probability of an arrhythmia exists then the detector 135 controls the stimulator 140 to stimulate the afferent nerves.

While monitoring of heart rate variability is currently preferred indication of the ratio sympathetic to parasympathetic nerve activity, with reference to the embodiment of FIG. 1, the comparator 130 may be any of a number of comparators, such as a summing amplifier, operational amplifier or other methods of comparing the levels of analog voltage signals. Furthermore, if the monitoring means 110 and 120 produce digital values reflecting the level of nerve activity then numerous methods known to one of skill in this art may be utilized to digitally compare the respective levels of nerve activity. As will be further appreciated by one of skill in the art, the comparator and detector means may be combined in a single electrical circuit such as a microprocessor, programmable logic array, etc.

operably associated with the detector 135 is a stimulator 140. Stimulator 140 acts to stimulate afferent nerves to the heart via lead 150 when the comparator 130 indicates that a high probability of an arrhythmia exists. As will be appreciated by those skilled in the art, various apparatus and methods of stimulating the afferent nerves exist. An example of an apparatus which may be employed to carry out the present invention is the NEUROCYBERNETIC PROSTHESIS™ System (manufactured by Cyberonics, Inc., Webster, Tex., USA), which consists of an implantable electrical pulse generator, an implantable helical bipolar stimulating lead electrode. See, e.g., W. Tarver et al., PACE 15, 1545 (1992) (See also J. Zabara, U.S. Pat. No. 4,867,164 and R. Terry, U.S. Pat. No. 4,979,511) (Applicant specifically intends that the disclosure of all United States Patent references cited herein be incorporated herein by reference).

Any suitable afferent nerve which is afferent to the central nervous system may be stimulated to carry out the present invention (i.e., nerves which are in the afferent division of the peripheral nervous system). The afferent nerve may be stimulated directly, or may be stimulated indirectly by means such as stimulating an organ or tissue (e.g., skin, muscle) from which the nerve projects. In general, the sensation of aching pain is transmitted by unmyelinated afferent nerve fibers (also known as type C nerve fibers or group IV nerve fibers, see A. Guyton, Textbook of Medical Physiology, 595 (1981)). Thus, to stimulate an afferent nerve fiber while minimizing any sensation of pain therefrom, the afferent nerve chosen may be one which is predominantly composed of myelinated nerve fibers, or the nerve may be stimulated in a manner which preferentially stimulates unmyelinated nerve fibers through proper choice of the frequency and intensity of stimulation, as is known to those skilled in the art. The afferent nerve may be one which enters the spinal column at thoracic levels T1 through T5. Particular nerves which may be stimulated include, but are not limited to, the vagus nerve and the median nerve.

Figure 2:
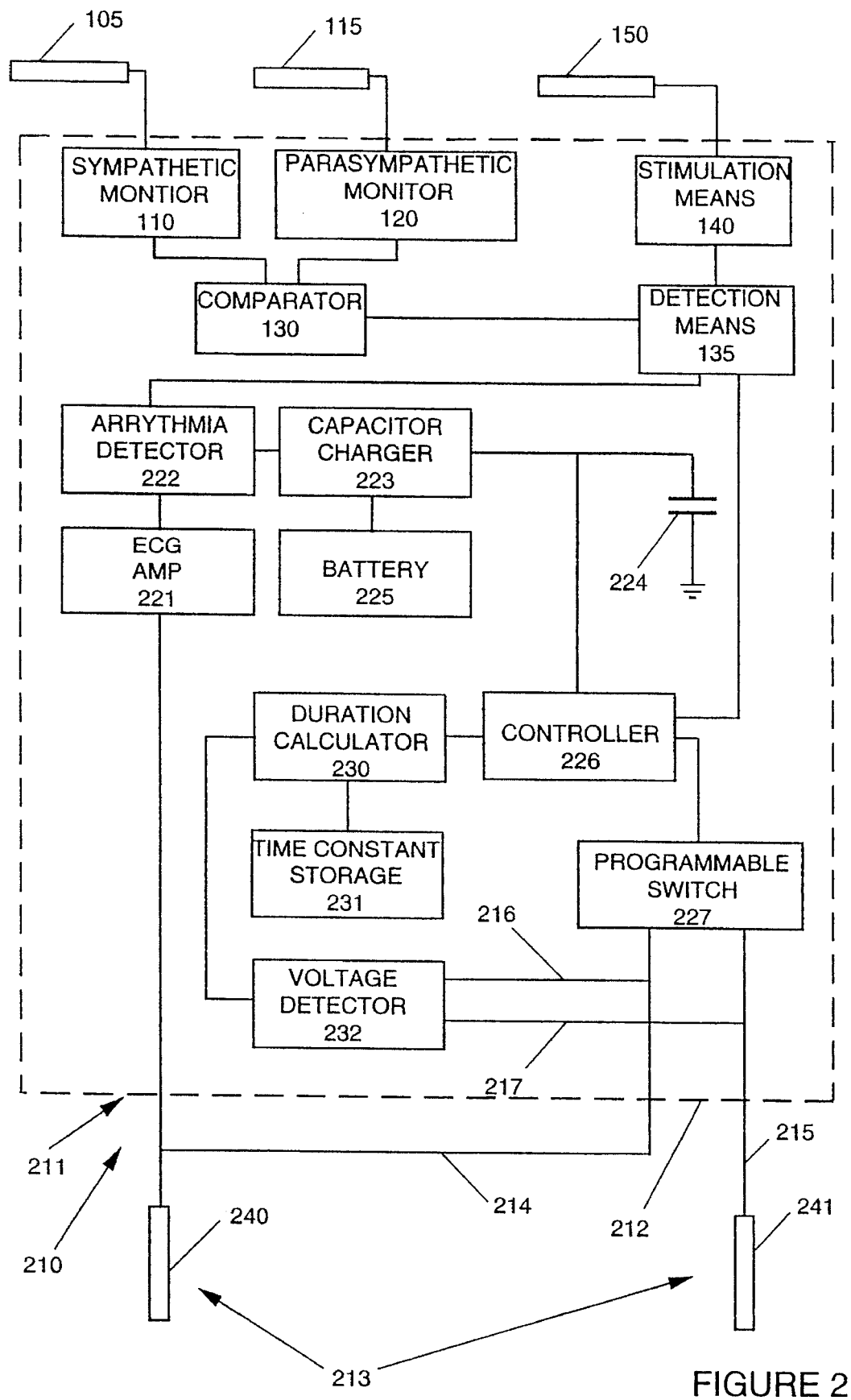
FIG. 2 schematically illustrates an apparatus according to the present invention for both the treatment and prevention of arrhythmia.

FIG. 2 illustrates another embodiment of the present invention wherein an implantable arrhythmia prevention apparatus further includes means for delivering electric pulse treatment to the heart in the event an arrhythmia occurs. FIG. 2 illustrates one manner in which an implantable arrhythmia treatment apparatus may be incorporated with the apparatus of FIG. 1. As shown in the schematic diagram of FIG. 2, one embodiment of the present invention comprises an implantable apparatus 210 for controlling cardiac arrhythmia. The apparatus according to the present invention includes an electronic circuit 211 contained within an implantable housing 212. Contained within the housing 212 are the monitors 110 and 120, the comparator 130, detector 135 and the stimulator 140. The leads 105, 115, and 150 are connected to their respective circuitry to sense sympathetic and parasympathetic nerve activity and to selectively stimulate afferent nerves. Operatively associated with the arrhythmia prevention circuity is electronic circuitry associated with arrhythmia treatment by electric pulse.

While a particular configuration circuitry for electric pulse treatment will now be described, as will be appreciated by those of skill in the art other circuitry for eclectic pulse treatment of arrhythmia may be utilized to achieve the advantages of the present invention.

In operation, the monitors 110 and 120 measure the level of activity of the sympathetic and parasympathetic nerves through leads 105 and 115. These levels of activity are then compared by the comparator 130 and the result supplied to the detector 135. If the presence of a high risk is detected, then the detector 135 activates the stimulator 140 to stimulate afferent nerves through lead 150 to prevent the arrhythmia. As seen in FIG. 2, the detector 135 may be further responsive to means for determining if the arrhythmia was prevented, such as the arrhythmia detector 222.

The electronic circuit 211 is connected by a series of leads 214 and 215 to an electrode configuration 213 including a series of electrodes positioned adjacent portions of the heart to provide an electric pulse to the heart to halt an occurring arrhythmia.

The electronic circuit 211 includes a conventional ECG amplifier 221 for amplifying sensed cardiac signals. The amplified cardiac signals are analyzed by a conventional arrhythmia detector 222 which determines if and what type of arrhythmia is present. The arrhythmia detector 222 may be one of several types well known to those skilled in the art and is preferably capable of distinguishing between high rate malignant tachycardia and ventricular fibrillation so as to deliver lower energy shocks in the former case than those to be delivered in the latter case.

A capacitor charging circuit 223, in response to a signal from the arrhythmia detector 222, charges the storage capacitor 224 to a predetermined voltage from the battery 225. The voltage may be selected prior to implantation of the apparatus 210 or may be dependent on the determination of the arrhythmia detector 222. The arrhythmia detector 222 may further act as discrimination means to determine the type of arrhythmia occurring, such as ventricular tachycardia. The discharge of the capacitor 224 is controlled by the controller 226, or multi-phasic circuit, such as described in U.S. Pat. No. 4,850,357. The capacitor 224 may be a single capacitor or a bank of parallel connected capacitors of equivalent capacity as would be readily understood by those skilled in the art. Power may be provided by any suitable means, such as a battery power source operably associated with the circuits in accordance with known techniques. Where a battery power source is used, that power source may be contained within the same container or housing 212 as the circuitry, or may be provided external to that housing, connected with suitable wires.

The controller 226 delivers electrical pulses to the electrodes through a programmable switch 227. As would be readily understood by those skilled in the art, the voltage waveform delivered by the capacitor 224 may be a decaying exponential waveform. The capacitor charger 223, capacitor 224, battery 225, controller 226 and programmable switch 227 thus form an electrical pulse generator for the apparatus 210.

Upon the generation of a voltage pulse, voltage detector 232 monitors the voltage at electrodes 240 and 241 through leads 216 and 217. This voltage is provided to the duration calculator 230 for determination of the time constant $t_s$ for the pulse. The time constant is determined by measuring the voltage at the electrodes 240 and 241 and determining the rate of change of the voltage at the electrodes 240 and 241. It will be understood by one of skill in this art that from the rate of change of the voltage at the electrodes 240 and 241, the time constant $t_s$ may be readily determined. It will be further understood by one of skill in the art that, while the embodiment of the present invention illustrated in FIG. 4 utilizes voltage detection to determine the time constant $t_s$, alternatively the current through the electrodes 240 and 241 could be measured and the time constant $t_s$ determined from the current. One method of measuring the current would be to place a low value of resistance in series with the electrodes 240 and 241 and measure the voltage across that resistance. This voltage is then directly proportional to the current through the electrodes. Once the time constant $t_s$ is determined the duration calculator 230 uses $t_s$ combined with the appropriate model time constant from the time constant storage 231 to determine the appropriate duration of the pulse.

The pulse duration information may then be transferred from the duration calculator 230 to the controller 226 which interrupts the pulse after the desired duration is reached by controlling programmable switch 227. As will be understood by one of skill in the art, the voltage detector 232, the duration calculator 230 and the time constant storage 231 may utilize electronic circuits known to one of skill in the art for measuring voltages, storing information and performing mathematical calculations. As will be further understood by one of skill in this art, the voltage detector 232, the duration calculator 230 and the time constant storage 231 may comprise a plurality of integrated circuits or may be incorporated into a single integrated circuit or may be incorporated into the electronic circuitry of the electric pulse generator described above.

With respect to the time constant storage 231, the values of the model time constant $t_m$ may be incorporated into the device at manufacture or may be programmed into the device at the time of implantation. Thus, the model time constant may be adjusted for each individual subject. Furthermore, the model time constant may be updated over time after implantation in a particular subject. The ability to update the model time constant after implantation would allow the device to compensate or adjust for variations over time of the subject's cardiac membrane RC time constant. Furthermore, one model time constant may be used for both monophasic and biphasic systems and for both pulses of hipbasic systems or individual model time constants may be utilized for the first and second pulses of a bipbasic system. In the present invention model time constants of from about 1 to about 4 milliseconds are preferred and from about 2.5 to about 3.5 milliseconds are more preferred.

A further aspect of the present invention involves placing the electrodes 240 and 241 in electrical contact with the heart, either directly or indirectly (e.g., by placing one electrode in the right ventricular cavity and one electrode in the superior vena cava). As will be appreciated by one of skill in this art, the number and location of the electrodes may be selected to increase the efficiency of the defibrillator, and more than two electrodes can be included if desired. One suitable placement of the electrode is described in U.S. Pat. No. 5,224,476, the disclosure of Which is incorporated by reference herein in its entirety. After placing the electrodes 240 and 241 and the electrode leads 214 and 215 in the subject, the RC model time $t_m$ constant may be determined for the subject and the electrode placement by determining the strength-duration relationship for defibrillation. Various external apparatus known to one of skill in this art may be connected to leads 214 and 215 for determining the model time constant. After determining the time constant it would then be stored in the implantable electric circuitry 211 in the time constant storage 231. Leads 105, 115, 150, 214 and 215 would then be connected to the electronics 211 and the device implanted in the subject.

As is shown in FIG. 2, the controller 226, may optionally be associated with the determining means 135 so as to control stimulation means 140 to stimulate the afferent nerves during application of the electric pulse. The stimulation of the afferent nerves during application of the electric pulse may be beneficial, for example, if said discrimination means in said arrhythmia detector 220 determines that the arrhythmia ventricular tachycardia. Furthermore, the determining means 135 may control the stimulation means 140 to continuously stimulate the afferent nerves to prevent reoccurrence of the arrhythmia even after application of an electric pulse.

The operation of the apparatus of FIG. 1 and FIG. 2 will now be described. In operation, monitor 110 monitors the sympathetic nerve activity of a subject while monitor 120 monitors the parasympathetic nerve activity of the subject. Comparator 130 compares the sympathetic and the parasympathetic nerve activity and provides the result of the comparison to detector 135. Detection 135 then determines if a high risk of arrhythmia in the subject exists based on the comparison of sympathetic and parasympathetic nerve activity. If such a high risk condition exists then stimulation means 140 stimulates afferent nerves in the subject to prevent the arrhythmia.

For the apparatus shown in FIG. 2, the arrhythmia detector 222 provides information to the detecting means 135 as to whether or not the stimulation has prevented an arrhythmia in the subject. In the event that an arrhythmia has occurred, the arrhythmia is halted by delivery of an electric pulse to the heart of the subject. The delivery of the electric pulse may be as described above, or through the utilization of other methods known to one of skill in the art for electric pulse treatment of heart arrhythmia. Methods and apparatus according to the present invention applicable for the prevention of arrhythmia may be combined with numerous forms of electric pulse treatment as, for example, anti-tachycardia pacing, large cardioversion and defibrillation shock.

In the event an arrhythmia has occurred, discrimination means within the arrhythmia detector 222 provides information to the detector 135 as to whether an occurring arrhythmia is ventricular tachycardia. The detector 135, in conjunction with the controller 226 then act as control means to control the stimulator 140 to stimulate the afferent nerves during the arrhythmia and, optionally, during the application of the electric pulse treatment. Optionally, the detector 135 may also be associated with the controller 226 to determine when the electric pulse has been delivered and to continuously stimulate the afferent nerves to prevent the reoccurrence of an arrhythmia after delivery of an electric pulse which halts the arrhythmia.

The foregoing is illustrative of the present invention, and is not to be construed as limiting thereof. The invention is defined by the following claims, with equivalents of the claims to be included therein.

That which is claimed is:

1. An implantable apparatus for combating heart arrhythmia in a subject, comprising:

means for monitoring a ratio of sympathetic nerve activity to parasympathetic nerve activity in said subject;

detection means for detecting a high risk of arrhythmia in said subject based on said ratio of sympathetic nerve activity to parasympathetic nerve activity; and an electrical stimulator operably associated with said detection means and responsive to said detection means for stimulating afferent nerves in said subject upon detection of a high risk of arrhythmia.

2. The apparatus of claim 1 further comprising:

determining means for determining whether or not said stimulation has prevented an arrhythmia in said subject;

electric pulse means operably associated with said determining means for transmitting at least one electrical pulse to said subject to halt an arrhythmia which has occurred by delivery of an electric pulse; and control means for controlling said electric pulse means to halt said arrhythmia when said determining means determines said stimulation did not prevent said arrhythmia.

3. The apparatus of claim 2 further comprising:

discrimination means responsive to said determining means for determining if an occurring arrhythmia is ventricular tachycardia; and wherein said control means controls said electrical stimulator to stimulate said afferent nerves when said discrimination means determines said arrhythmia is ventricular tachycardia.

4. The apparatus of claim 2 wherein said electrical stimulator includes means for continuously stimulating said afferent nerves to prevent a reoccurrence of an arrhythmia after delivery of said electric pulse.

5. The apparatus of claim 2 wherein said electric pulse means comprises means for halting said arrhythmia selected from the group consisting of anti-tachycardia pacing, large cardioversion, and defibrilation shock.

6. An apparatus according to claim 1, wherein said means for monitoring the ratio of sympathetic nerve activity to parasympathetic nerve activity in said subject comprises means for monitoring heart rate variability in said subject.

7. The apparatus of claim 1 wherein said apparatus is sealed in a sterile container.

8. An apparatus according to claim 1, wherein said means for monitoring the ratio of sympathetic nerve activity to parasympathetic nerve activity in said subject comprises:

first monitoring means for monitoring sympathetic nerve activity in said subject;

second monitoring means for monitoring parasympathetic nerve activity in said subject;

comparing means connected to said first and second monitoring means for providing a comparison of said sympathetic and said parasympathetic nerve activity;

at least two monitoring leads electrically connected to said first and second monitoring means; and a stimulating lead electrically connected to said electrical stimulator and contacting said subject for transmitting the stimulation from said electrical stimulator to the afferent nerves of said subject.

9. A method of combating heart arrhythmia in a subject comprising:

monitoring a ratio of sympathetic nerve activity to parasympathetic nerve activity in said subject;

detecting a high risk of arrhythmia in said subject based on the ratio of sympathetic and parasympathetic nerve activity; and stimulating afferent nerves in said subject upon detection of a high risk of arrhythmia.

10. The method of combating heart arrhythmia of claim 9, said method further comprising:

determining whether or not said stimulation has prevented an arrhythmia in said subject; and halting an arrhythmia which has occurred by delivery of an electric pulse when said stimulation has not prevented the arrhythmia.

11. The method of combating heart arrhythmia of claim 10 further comprising:

determining if an occurring arrhythmia is ventricular tachycardia; and stimulating the afferent nerves during occurrence of the arrhythmia when the arrhythmia is ventricular tachycardia.

12. The method of combating heart arrhythmia of claim 10 further comprising:

continuously stimulating the afferent nerves to prevent a reoccurrence of an arrhythmia after delivery of an electric pulse to halt the arrhythmia.

13. The method of combating heart arrhythmia of claim 10 wherein the electric pulse for halting the arrhythmia is selected from the group comprising anti-tachycardia pacing, large cardioversion and defibrillation shock.

14. A method according to claim 9, wherein said step of monitoring the ratio of sympathetic nerve activity to parasympathetic nerve activity in said subject is carried out by monitoring heart rate variability in said subject.

15. An implantable apparatus for combating heart arrhythmia in a subject, comprising:

(a) monitoring means for monitoring sympathetic nerve activity and parasympathetic nerve activity, wherein said monitoring means monitors a ratio of said sympathetic nerve activity to said parasympathetic nerve activity, said monitoring means comprising;

first monitoring means for monitoring sympathetic nerve activity in said subject;

second monitoring means for monitoring parasympathetic nerve activity in said subject;

comparing means connected to said first and second monitoring means for comparing the ratio of sympathetic nerve activity to parasympathetic nerve activity;

(b) detection means for detecting a high risk of arrhythmia in said subject based on the ratio of nerve activity; and (c) an electrical stimulator operably associated with said subject and said detection means and responsive to said detection means for stimulating afferent nerves in said subject upon detection of a high risk of arrhythmia.

16. A method of combating heart arrhythmia in a subject, comprising:

(a) monitoring the sympathetic nerve activity in said subject;

(b) monitoring the parasympathetic nerve activity in said subject;

(c) comparing said sympathetic nerve activity to said parasympathetic nerve activity to provide a ratio of said sympathetic nerve activity to said parasympathetic activity;

(d) detecting a high risk of arrhythmia in said subject based on the ratio of sympathetic and parasympathetic nerve activity; and (e) stimulating afferent nerves in said subject upon detection of a high risk of arrhythmia.

\* \* \* \* \*

UNITED STATES PATENT AND TRADEMARK OFFICE
CERTIFICATE OF CORRECTION

PATENT NO. : 5,522,854
DATED : 4 June, 1996
INVENTOR(S) : Ideker, et al.

It is certified that error appears in the above-identified patent and that said Letters Patent is hereby corrected as shown below:

Item [75],

On the cover page, change the inventor's name from "Xiaohong Xhou" to -- Xiaohong Zhou --

Signed and Sealed this

Twenty-fourth Day of September, 1996

*Attest:*

BRUCE LEHMAN

*Attesting Officer*     *Commissioner of Patents and Trademarks*